(12) United States Patent
Lee et al.

(10) Patent No.: US 10,058,335 B2
(45) Date of Patent: Aug. 28, 2018

(54) MODULARIZED PATIENT-SPECIFIC REGISTRATION GUIDE AND SYSTEM USING SAME

(71) Applicant: SNU R&DB FOUNDATION, Seoul (KR)

(72) Inventors: Kun Woo Lee, Seoul (KR); Tae Ho Jang, Seoul (KR)

(73) Assignee: SNU R&DB FOUNDATION, Seoul (KR)

( * ) Notice: Subject to any disclaimer, the term of this patent is extended or adjusted under 35 U.S.C. 154(b) by 334 days.

(21) Appl. No.: 14/766,431

(22) PCT Filed: Feb. 7, 2013

(86) PCT No.: PCT/KR2013/001007
§ 371 (c)(1),
(2) Date: Aug. 6, 2015

(87) PCT Pub. No.: WO2014/123263
PCT Pub. Date: Aug. 14, 2014

(65) Prior Publication Data
US 2015/0374384 A1    Dec. 31, 2015

(51) Int. Cl.
*A61F 5/00* (2006.01)
*A61B 17/15* (2006.01)
(Continued)

(52) U.S. Cl.
CPC ........ *A61B 17/154* (2013.01); *A61B 17/1764* (2013.01); *A61B 90/39* (2016.02);
(Continued)

(58) Field of Classification Search
None
See application file for complete search history.

(56) References Cited

U.S. PATENT DOCUMENTS

2002/0133163 A1    9/2002 Axelson et al.
2006/0190090 A1*   8/2006 Plaskon .............. A61F 2/30721
                                                      623/22.36
(Continued)

FOREIGN PATENT DOCUMENTS

KR    10-2008-0113960 A    12/2008
WO    WO 2012/169642 A1    12/2012

OTHER PUBLICATIONS

PCT International Search Report, PCT/KR2013/001007, dated Nov. 5, 2013, 6 Pages.

*Primary Examiner* — Sameh Boles
(74) *Attorney, Agent, or Firm* — Fenwick & West LLP

(57) ABSTRACT

The present invention relates to a modularized patient-specific registration guide and a system using the same and, more specifically, to a modularized patient-specific registration guide capable of rapidly carrying out an initial registration step for a bone, which is a surgical site, and inducing a registration step to be easily performed even during an operation, and a system using the same. The modularized patient-specific registration guide, according to one embodiment of the present invention, is a registration guide manufactured according to a three-dimensional shape of a bone obtained in an imaging device, the registration guide comprising: a first member having one or more markers and one or more extending parts that come in contact with the bone, and having a groove on one side thereof; and a second member accommodated in or separable from the groove of the first member and having one or more markers.

10 Claims, 3 Drawing Sheets

(51) Int. Cl.
  *A61B 17/17* (2006.01)
  *A61B 90/00* (2016.01)
  *A61B 34/20* (2016.01)

(52) U.S. Cl.
  CPC .............. *A61B 2034/2055* (2016.02); *A61B 2090/3916* (2016.02); *A61B 2090/3983* (2016.02)

(56) References Cited

U.S. PATENT DOCUMENTS

| | | |
|---|---|---|
| 2008/0161815 A1 | 7/2008 | Schoenefeld et al. |
| 2009/0024131 A1 | 1/2009 | Metzger et al. |
| 2010/0137869 A1 | 6/2010 | Borja et al. |
| 2010/0174378 A1 | 7/2010 | Metzger et al. |
| 2010/0222889 A1 | 9/2010 | Howling et al. |
| 2011/0015639 A1 | 1/2011 | Metzger et al. |
| 2011/0054478 A1 | 3/2011 | Vanasse et al. |
| 2011/0060341 A1 | 3/2011 | Angibaud et al. |
| 2011/0071533 A1 | 3/2011 | Metzger et al. |
| 2011/0093108 A1 | 4/2011 | Ashby et al. |
| 2011/0106093 A1 | 5/2011 | Romano et al. |
| 2011/0184525 A1 | 7/2011 | Hagen |
| 2011/0218545 A1 | 9/2011 | Catanzarite et al. |
| 2011/0257653 A1* | 10/2011 | Hughes .................. A61B 34/20 606/79 |
| 2014/0096369 A1 | 4/2014 | Matsumoto et al. |

* cited by examiner

MODULARIZED PATIENT-SPECIFIC REGISTRATION GUIDE AND SYSTEM USING SAME

TECHNICAL FIELD

The present disclosure relates to a modularized patient-specific registration guide and a system using the same, and more particularly, to a modularized patient-specific registration guide that allows for rapid performance of an initial registration process of a target bone and induces easy performance of a registration process during surgery, and a system using the same.

BACKGROUND ART

Total knee replacement is a surgical procedure to replace an inflamed or damaged cartilage or bone in the knee with an artificial joint when it is difficult to restore to a normal state, and includes processes of cutting both ends of the femur and tibia and implanting an artificial joint.

The conventional total knee replacement surgery has low precision because it involves cutting a patient's bone depending on a surgeon's experience and skills. To solve the problem, a cutting method using robots and a cutting method using optical infrared marker tracking is now widely used, and these methods involve a registration process for measuring a relative location between a target bone and a cutting device and a posture to increase the cutting accuracy and precision.

However, the registration process is not a process essential to achieving the primary purpose of surgery, i.e., cutting the real bone and implanting the artificial joint, and it is merely an ancillary process for helping achieve the purpose, but to improve the accuracy of surgery, it is inevitably performed through a complex procedure of about 15-20 minutes.

Registration is performed by indicating about 40 anatomical feature points of the femur and tibia using a probe, and in this instance, many errors occur, which often results in an incorrect registration result or registration failure.

During the registration process, the patient's knee joint is exposed through an incision, and the hazard of consequential secondary inflammation greatly increases and unnecessary bleeding continues. Furthermore, in the case of the cutting method using optical infrared marker tracking, one or two rods with infrared markers should be directly implanted into each of the femur and tibia of the patient, so there is a risk of fractures at the corresponding parts later.

Accordingly, there is a need for a new registration method that has a reduced error in registration, is convenient to use, and reduces the time it takes.

DISCLOSURE

Technical Problem

The present disclosure is directed to providing a modularized patient-specific registration guide that may rapidly induce the registration of the coordinates of a patient's bone and the coordinates of a robot for surgery by pre-recognizing relationship information between the bone and the registration guide through a marker of the registration guide, and a system using the same.

Technical Solution

To achieve the object, a modularized patient-specific registration guide according to an exemplary embodiment of the present disclosure, which is manufactured to conform to a three-dimensional (3D) shape of a bone obtained by an imaging equipment, includes a first member having at least one marker, at least one extension part which comes in close contact with the bone, and a groove on one side, and a second member which is receivable in or separable from the groove of the first member, the second member having at least one marker.

The second member may have at least one through-hole to be fixed to the bone with a bolt.

The marker may have a protruding or recessed shape from a surface of the first member or the second member.

The marker may be formed such the marker passes through a partial area of the first member or the second member.

The marker may be an optical marker for optical tracking.

A ring made of metal may be inserted and fixed in the through-hole of the second member.

A modularized patient-specific registration guide system according to an exemplary embodiment of the present disclosure includes a robot for surgery, an imaging equipment to obtain data associated with a 3D shape of a target bone, a guide manufacturing apparatus to manufacture a registration guide to conform to the 3D shape of the bone obtained by the imaging equipment, and a registration guide manufactured by the guide manufacturing apparatus, wherein the registration guide includes a first member having at least one marker, at least one extension part which comes in close contact with the bone, and a groove on one side, and a second member which is receivable in or separable from the groove of the first member, the second member having at least one marker, and relationship information between coordinates of the bone obtained when manufacturing the registration guide and coordinates of the marker is pre-inputted to the robot for surgery, relationship information between coordinates of the robot for surgery and the coordinates of the marker is derived through measurement, and the robot for surgery registers the coordinates of the robot for surgery and the coordinates of the bone.

The second member may have at least one through-hole to be fixed to the bone with a bolt.

A ring made of metal may be inserted and fixed in the through-hole of the second member.

The guide manufacturing apparatus may be a rapid prototyping apparatus.

Advantageous Effects

The modularized patient-specific registration guide and system of the present disclosure has an improvement effect of registration precision because the registration guide is manufactured to conform to an actual bone shape of a patient.

Also, the modularized patient-specific registration guide and system of the present disclosure has a dramatic reduction effect of the time and efforts taken to register the coordinates of a patient's bone and the coordinates of a robot for surgery because relationship information between the bone and the guide is recognized beforehand.

Furthermore, the modularized patient-specific registration guide and system of the present disclosure has a facilitation effect for a registration process during surgery as well as an initial registration process.

BEST MODE

Hereinafter, a modularized patient-specific registration guide according to the preferred embodiments of the present disclosure will be described in detail with reference to the accompanying drawings.

Figure 1:
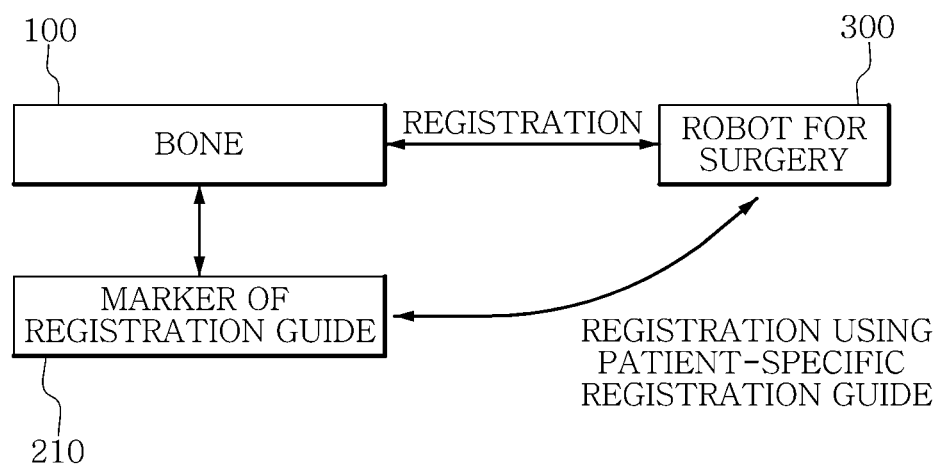
FIG. 1 is a diagram illustrating an operation process of a modularized patient-specific registration guide system according to an exemplary embodiment of the present disclosure.

FIG. 1 is a diagram illustrating an operation process of a modularized patient-specific registration guide system according to an exemplary embodiment of the present disclosure.

Referring to FIG. 1, the modularized patient-specific registration guide system of the present disclosure acquires, for registration of the coordinates of a bone 100 and the coordinates of a robot 300 for surgery, relationship information between the coordinates of the bone 100 and a marker 210 of a registration guide and relationship information between the coordinates of the robot 300 for surgery and the marker 210 of the registration guide by measurement, and from the relationship information, registration of the coordinates of the bone 100 and the coordinates of the robot 300 for surgery is performed.

The relationship information between the coordinates of the bone 100 and the marker 210 of the registration guide is information that may be pre-acquired when manufacturing the registration guide, and the relationship information between the coordinates of the robot 300 for surgery and the marker 210 of the registration guide is information that may be acquired quickly by measurement, and thus, according to the present disclosure, registration of the coordinates of the bone 100 and the coordinates of the robot 300 for surgery may be rapidly performed.

To manufacture the registration guide, data associated with a three-dimensional (3D) shape of the target bone 100 is pre-acquired through imaging equipment (not shown). The imaging equipment provides, for example, radiography (X-ray) images, computer tomography (CT) images or magnetic resonance imaging (MRI), and from the CT or MRI image, the shape of a target site, the patient's femur and tibia may be obtained. Subsequently, a guide manufacturing apparatus (not shown) manufactures the registration guide having the marker 210 based on the 3D image of the bone obtained by the imaging equipment. The guide manufacturing apparatus may be, for example, a rapid prototyping apparatus.

Subsequently, the registration guide manufactured by the guide manufacturing apparatus is attached to the target bone 100, and as described above, relationship information between the coordinates of the bone 100 and the marker 210 of the registration guide and relationship information between the coordinates of the robot 300 for surgery and the marker 210 of the registration guide by measurement is acquired, and from the relationship information, registration of the coordinates of the bone 100 and the coordinates of the robot 300 for surgery is performed. When the registration is performed, information associated with a relative location between the target bone 100 and the robot 300 for surgery and a posture is calculated.

Figure 2A:
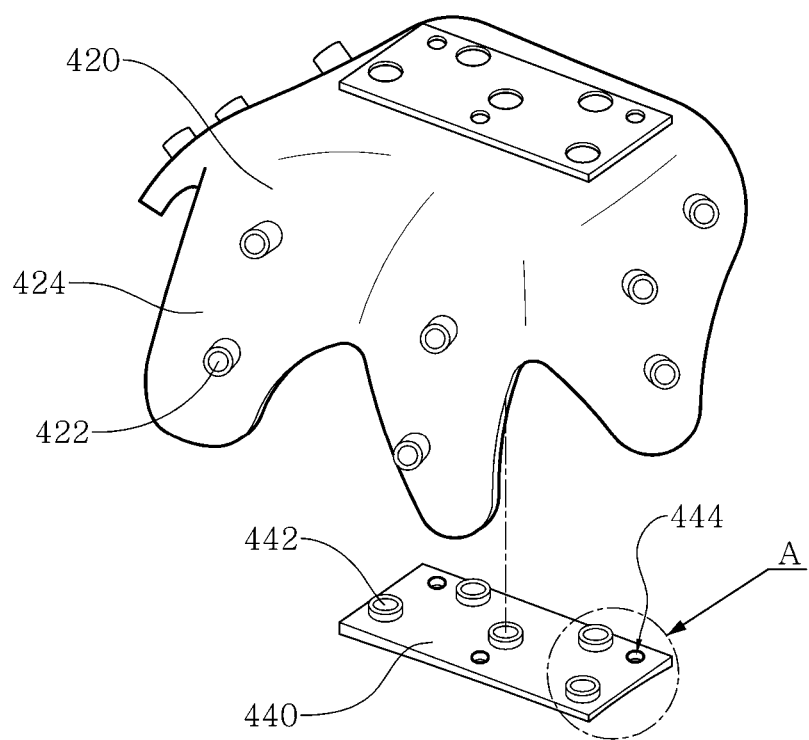
FIG. 2a is an exploded perspective view of a modularized patient-specific registration guide according to an exemplary embodiment of the present disclosure.
Figure 2B:
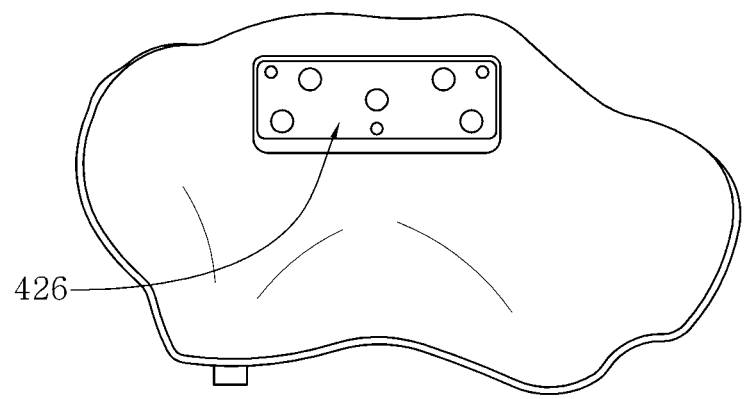
FIG. 2b is a plan view of a first member of FIG. 2a as viewed from the bottom.

FIG. 2a is an exploded perspective view of the modularized patient-specific registration guide according to an exemplary embodiment of the present disclosure, and FIG. 2b is a plan view of the first member of FIG. 2a as viewed from the bottom.

Referring to FIGS. 2a and 2b, the registration guide 400 includes a first member 420 and a second member 440.

The registration guide 400 of the present disclosure is manufactured to conform to the 3D shape of the bone obtained by the imaging equipment as described above. To cause the manufactured registration guide 400 to come in close contact with the bone, the first member 420 has at least one extension part 424. The shape and number of the extension part 424 may be variously modified in consideration the shape of the bone 100 and easiness of production.

Also, the first member 420 includes at least one marker 422 that serves as a recognition marker for the robot 300 for surgery during a registration process. The marker 422 protrudes from the surface of the first member 420, and may be formed in a protrusive shape, for example, a cylindrical shape. The extension part 424 and the marker 422 of the first member 420 may be integrally formed by one molding process.

Also, the marker 422 is not limited to the shape shown in FIG. 2, and may be formed, for example, such that the marker 422 is recessed from the surface of the first member 420 or the second member 440, or such that the marker 422 passes through a partial area of the first member 420 or the second member 440. Further, the marker 422 may be formed of an optical marker for optical tracking.

The first member 420 and the second member 440 of the registration guide 400 of the present disclosure have a modularized shape allowing assembly and disassembly. That is, the first member 420 has a groove 426 on one side, where the second member 440 may be received or separated.

When the second member 440 is received in the groove 426 of the first member 420, an initial registration process may be performed by attaching the registration guide 400 to the target bone, and after the initial registration, the first member 420 is separated from the second member 440 and only the second member 440 may remain on the bone. To maintain the fixed condition of the second member 440 to the bone after the first member 420 is separated, various fixing methods such as screw fastening and adhesive application may be used, but in this embodiment, a through-hole 444 is formed in the second member 440, and when a bolt passes through through-hole 444, the second member 440 is screw-connected to the bone.

Figure 3:
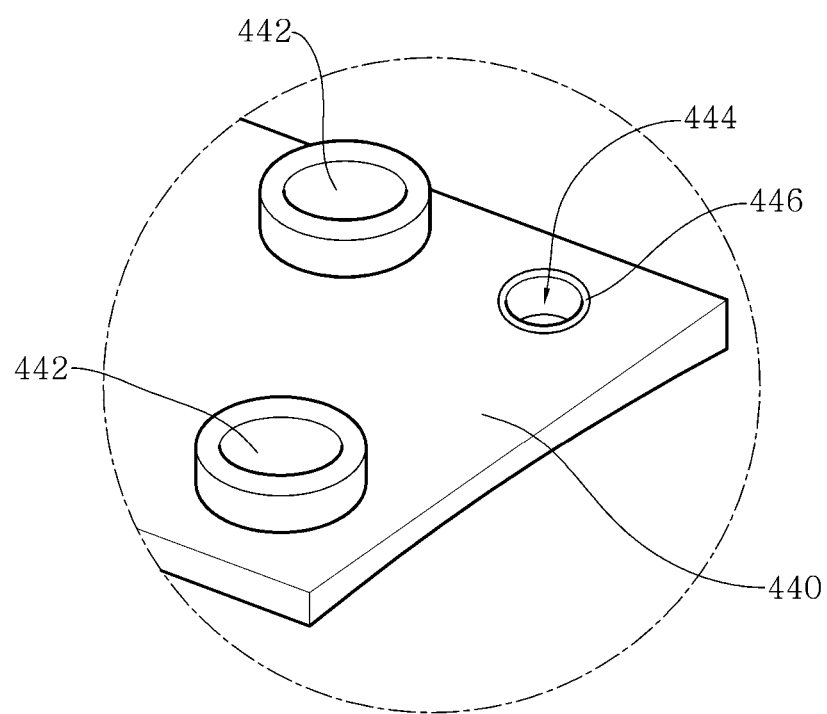
FIG. 3 is a partial perspective view of a second member of a modularized patient-specific registration guide of the present disclosure.

FIG. 3 is a partial perspective view of the second member of the modularized patient-specific registration guide of the present disclosure.

Referring to FIG. 3, a ring 446 made of metal is inserted and fixed in the through-hole 444 of the second member 440. The registration guide 400 of the present disclosure is made of a soft material to minimize damage to the bone during a process of attaching it to the target bone arbitrarily, a registration process, and a removal process, so there is a likelihood that the through-hole 444 of the second member 440 insufficiently performs a guide function for the bolt when fixing the second member 440 to the bone through drilling. Thus, during drilling, to reinforce the guide function for the bolt, the metal ring 446 is inserted into the through-hole 444 of the second member 440, thereby the bolt may pass straight through the through-hole 444 without causing shape deformation of the through-hole 444.

Figure 4:
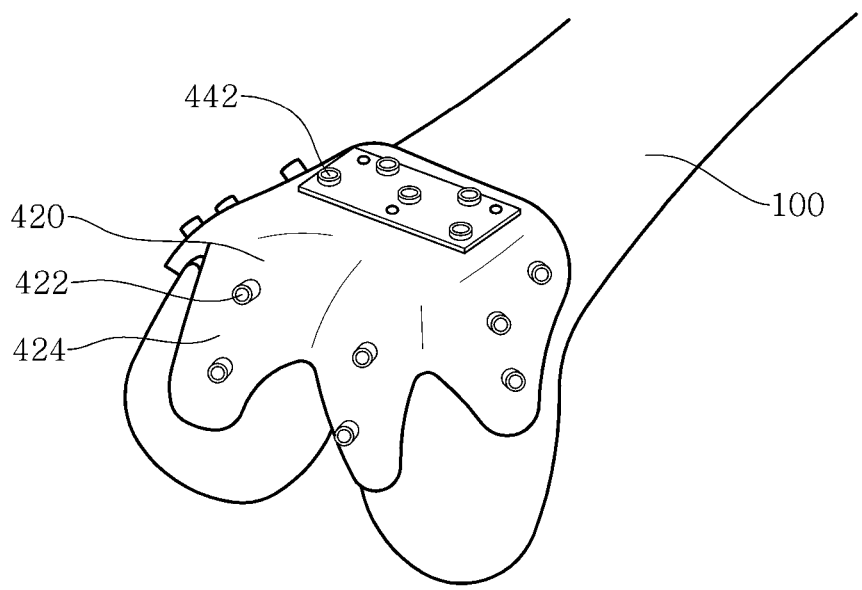
FIG. 4 is a diagram showing a modularized patient-specific registration guide of the present disclosure attached to a bone.
Figure 5:
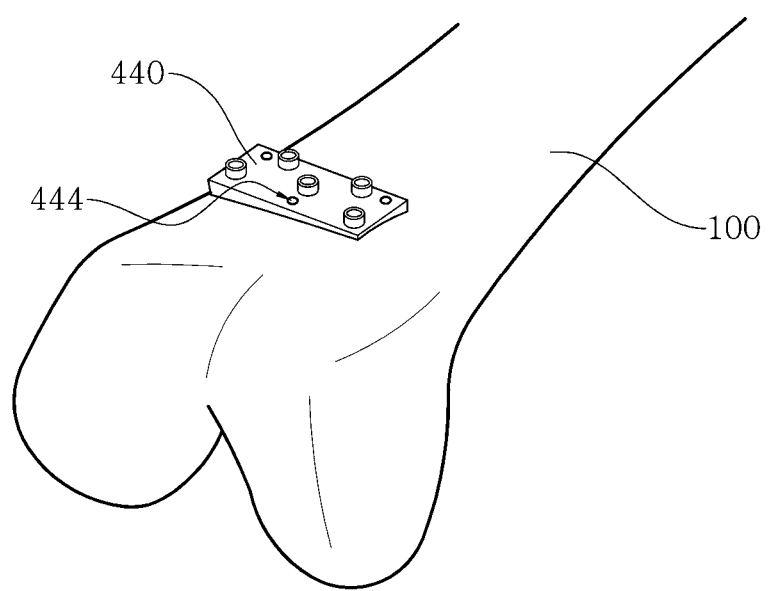
FIG. 5 is diagram showing a modularized patient-specific registration guide of the present disclosure from which a first member has been removed.

FIG. 4 is a diagram showing the modularized patient-specific registration guide of the present disclosure attached to the bone, and FIG. 5 is diagram showing the modularized patient-specific registration guide of the present disclosure from which the first member has been removed.

Referring to FIGS. 4 and 5, as the second member 440 is received in the groove 426 of the first member 420, the first member 420 and the second member 440 in integrated form are attached to the bone 100. Because the first member 420 and the second member 440 have the markers 422 and 442, the robot 300 for surgery recognizes the markers 422 and 442 and performs an initial registration process.

After the initial registration, to proceed with surgery including cutting the bone 100, the first member 420 is removed from the bone 100, and auxiliary instruments for surgery including cutting are attached to the position of the first member 420. In this instance, because the second member 440 is in fixed condition to the bone 100 with the bolt, the second member 440 still remains on the bone 100 separately from the first member 420.

Thus, the registration guide 400 of the present disclosure may continuously provide location information of the bone 100 by the marker 442 of the second member 420 after the initial registration, so the registration guide 400 has a benefit of providing information necessary for registration in real time during surgery.

The registration guide and system according to the present disclosure may accurately indicate a target site or assist cutting to conform to a bone shape of a patient, and may be thus used in nearly all types of surgery related to bones as well as all orthopaedic surgery using artificial joints, such as, for example, total hip replacement, total elbow replacement, and total ankle replacement.

While the preferred embodiments of the present disclosure have been described hereinabove, the present disclosure is not limited thereto, and it should be understood that the present disclosure may be modified and embodied in various forms within the scope of the appended claims, the detailed description of the invention, and the accompanying drawings, and such modifications fall within the scope of the present disclosure.

The invention claimed is:

1. A modularized patient-specific registration guide which is manufactured to conform to a three-dimensional (3D) shape of a bone obtained by an imaging equipment, the modularized patient-specific registration guide comprising:
a first member having at least one marker on a first side of the first member, at least one extension part that extends from the first member to conform to a shape of the bone, and a groove on a second side of the first member that is under the first side of the first member, the at least one marker of the first member extending from the first side of the first member to form a protrusion or a recessed shape and the at least one marker of the first member indicative of a first location of the bone that is input to a robot for surgery on the bone; and
a second member which is in contact with the bone and is configured to attach to the groove of the first member, the second member having at least one marker extending from the second member to form a protrusion or recessed shape indicative of a second location of the bone that is input to the robot for surgery on the bone, wherein the at least one marker of the second member passes through the first member.

2. The modularized patient-specific registration guide according to claim 1, wherein the second member has at least one through-hole, the second member fixed to the bone with a bolt through the at least one through-hole.

3. The modularized patient-specific registration guide according to claim 1, wherein the marker has a protruding or recessed shape from the first side of the first member or a side of the second member.

4. The modularized patient-specific registration guide according to claim 1, wherein the marker passes through a partial area of the first member or the second member.

5. The modularized patient-specific registration guide according to claim 1, wherein the marker is an optical marker for optical tracking.

6. The modularized patient-specific registration guide according to claim 1, wherein a ring made of metal is inserted and fixed in the through-hole of the second member.

7. A modularized patient-specific registration guide system, comprising:
a robot for surgery;
an imaging equipment to obtain data associated with a three-dimensional (3D) shape of a target bone;
a guide manufacturing apparatus to manufacture a registration guide to conform to the 3D shape of the target bone obtained by the imaging equipment; and
a registration guide manufactured by the guide manufacturing apparatus,
wherein the registration guide comprises:
a first member having at least one marker on a first side of the first member, at least one extension part that extends from the first member to conform to a shape of the bone, and a groove on a second side of the first member that is under the first side of the first member, the at least one marker of the first member extending from the first side of the first member to form a protrusion or a recessed shape and the at least one marker of the first member indicative of a first location of the bone that is input to the robot for surgery on the target bone; and
a second member which is in contact with the target bone and is configured to attach to the groove of the first member, the second member having at least one marker extending from the second member to form a protrusion or recessed shape indicative of a second location of the target bone that is input to the robot for surgery on the target bone, wherein the at least one marker of the second member passes through the first member, and
relationship information between coordinates of the target bone obtained when manufacturing the registration guide and coordinates of the marker of the first member and the marker of the second member is pre-inputted to the robot for surgery, relationship information between coordinates of the robot for surgery and the coordinates of the marker of the first member and the marker of the second member is derived through measurement, and the robot for surgery registers the coordinates of the robot for surgery and the coordinates of the target bone.

8. The modularized patient-specific registration guide system according to claim 7, wherein the second member has at least one through-hole, the second member fixed to the bone with a bolt through the at least one through-hole.

9. The modularized patient-specific registration guide system according to claim 7, wherein a ring made of metal is inserted and fixed in the through-hole of the second member.

10. The modularized patient-specific registration guide system according to claim 7, wherein the guide manufacturing apparatus is a rapid prototyping apparatus.

* * * * *